United States Patent [19]
Savolainen

[11] Patent Number: 5,262,307
[45] Date of Patent: Nov. 16, 1993

[54] PROCEDURE FOR HYDROLYZING KERATIN

[75] Inventor: Jouko E. T. Savolainen, Kauniainen, Finland

[73] Assignee: Biodata Oy, Helsinki, Finland

[21] Appl. No.: 834,590

[22] Filed: Feb. 12, 1992

[30] Foreign Application Priority Data

Feb. 14, 1991 [FI] Finland ................. 910722

[51] Int. Cl.⁵ ............................ G12P 21/06
[52] U.S. Cl. .................................. 435/68.1
[58] Field of Search ........................ 435/68.1

[56] References Cited

U.S. PATENT DOCUMENTS

| | | | |
|---|---|---|---|
| 4,279,996 | 7/1981 | Yoshioka et al. | 435/68.1 |
| 4,324,805 | 4/1982 | Olsen | 435/68.1 |
| 4,948,876 | 8/1990 | Bore | 435/68.1 |

FOREIGN PATENT DOCUMENTS

| | | |
|---|---|---|
| 2705669 | 8/1978 | Fed. Rep. of Germany . |
| 3305305 | 8/1983 | Fed. Rep. of Germany . |

*Primary Examiner*—Herbert J. Lilling
*Attorney, Agent, or Firm*—Willian Brinks Olds Hofer Gilson & Lione

[57] ABSTRACT

The present invention relates to a procedure for hydrolyzing keratin, in which procedure the solid keratin ingredient is (a) pretreated with an aqueous solution containing sulphite ions to form denatured keratin, and (b) hydrolyzed with the aid of a proteolytic enzyme to form keratin hydrolysate. The pretreatment is carried out at about 60° to 100° C. and it lasts about 10 minutes to 4 hours. The hydrolysate thus obtained can be treated further for use as a fodder addition or to isolate oligopeptides for use in cosmetics.

19 Claims, No Drawings

PROCEDURE FOR HYDROLYZING KERATIN

The invention relates to a procedure for hydrolyzing keratin, in which procedure solid keratin material is pretreated in an aqueous solution containing sulphite ions to form denatured keratin, then and hydrolyzed with the aid of a proteolytic enzyme to form keratin hydrolysate. In the present context, substances containing keratin are feathers, hair, wool, bristles, horsehair, horns, cloven hooves, and hooves. Most of these, such as feathers and hair, are almost worthless as such in the industrial sense, and when wasted in great masses, are problematic even though they decompose in nature.

With the procedure of the invention, keratin can be hydrolyzed into a hydrolysate which animals are able to make use of, e.g., fodder protein can be enriched with the hydrolysate.

Oligopeptides of a given length can be produced from hydrolysates for ingredients used in cosmetic products, and specifically, for treating and caring the skin and hair.

It is known that the hydrolyzability and melting of keratin-containing byproducts, e.g. feathers and hair, are enhanced when treating them physically, that is, with heat, for example, at 146° C. and at 345 kPa for 30 to 70 minutes. This so-called denaturation leads to a change in the structure of the keratin so that the sulphur bridges which provide the keratin with a chemically enduring structure become open, whereby the enzymes, including the digestive enzymes of the animals, can hydrolyze the denatured keratin into useful smaller ingredients, i.e. peptides.

A drawback of the procedure is the partial destruction of certain amino acids and production of artificial amino acids, for instance lantionine, thus decreasing the quality of the product.

On the other hand, a chemical treatment is also known in the art for opening the sulphur bridges and for chopping the protein into smaller parts, that is, into peptides. The treatment of keratin at $\leq 2.0$ to 4.0 pH, at the boiling temperature for 2 to 20 hours opens the sulphur bridges of the keratin and chops the keratin into polypeptides and oligopeptides, and even into free amino acids.

Similarly, a treatment within a highly alkaline range at the boiling temperature, and even higher, for over two hours, yields the same result as mentioned above.

A drawback of the chemical treatment is the partial, or even complete destruction of certain amino acids and a highly variable size of the peptides included in the hydrolysate thus produced. The chemical hydrolysis, particularly on the alkaline side, yields artificial amino acids, lanthionine and lysinoalanine, which may be toxic.

By hydrolyzing the keratin enzymatically and by a requisite pretreatment, both taking place under mild conditions, a number of advantages are gained in comparison with the above-described methods.

The enzymatic hydrolysis requires denaturation of keratin, that is, such treatment of the native keratin that the sulphur bridges open, either all or only a certain part of them, so that the proteolytic or keratolytic enzyme is able to hydrolyze the peptide bonds of the keratin and to chop the keratin into peptides.

The pretreatment, i.e. denaturation, can be carried out physically, that is, by thermal treatment, or chemically in acid or alkaline environment, as described above, or in another chemical manner in conjunction with the hydrolysis, though under milder conditions.

DE-patent No. 2705669 describes an enzymatic keratin hydrolysis in which hair and wool were treated, their amount being about 7% of the matter in an aqueous mixture. The denaturation takes place at 1.5 to 2.0 pH, at $\geq 80°$ C., for at least 4 hours. Thereafter the keratin-containing matter, that is, hair and wool, was water-washed.

In DE-patent No. 3305305, an oxidative sulphitolysis is used in the denaturation, wherein the cystine of the keratin forms, together with sulphite, a keratin cysteine sulphonate and a keratin cysteine. The keratin cysteine thus produced is oxidized in the presence of a sulphite with a thionate, e.g. tetrathionate, into keratin cysteine sulphonate. The total reaction is as follows:

$$\text{kerat-S-S-kerat plus } 2 + 2\,SO_3^{-2} + S_4O_6^{-2}$$

$$2\,\text{kerat-S-SO}_3^- + 2\,S_2O_3^-$$

The same reaction is also presented by Bailey & Cole in the publication J- Biol. Chem. 234. 17133–1739, 1959. As disclosed in the patent, the pretreatment was carried out as follows: 100 g of chopped wool were treated in 3.5 liter water, the concentration being <3%, with about 27% $NaHSO_3$ and about 24% $Na_2S_4O_6$, at 9 pH and at about 40° C. The treatment time was 15 hours. After the treatment the wool was washed in abundant water.

The actual hydrolysis is carried out after the denaturation and wash with the aid of protease enzymes under mild conditions.

The hydrolysis the disclosed in the DE-patent No. 2705669, was carried out as follows. The pretreated keratin-containing matter, i.e. hair or wool, was mixed at a 7% concentration in 95 liters water. The temperature was maintained at 50 to 55° C. and the pH at 9.5. The mixture was stirred. A certain amount of urea and ammonium sulphate were added into the mixture. For controlling the pH, ammonia was used. The time of hydrolysis was 10 to 20 hours. For the enzyme, Bacillus proteases were employed. Upon the completed hydrolysis, the mixture was heated to 95° C. in order to destroy the enzymatic activity. The hydrolysate was filtered and the solution dried. The average molecular weight of the hydrolysate was 1000 to 3000.

The hair pretreated according to the hydrolysis disclosed in the DE-patent No. 3305305 was mixed in 3.0 liter of enzyme solution at a 3.4% concentration. The pH was balanced to 9 with ammonia, and the temperature was maintained at 40° C. For the enzyme, a commercial protease was used. The mixture was stirred evenly all the time. The hydrolyzing time was 3 hours. At the end of the hydrolysis, the hydrolysate was filtered, whereby the remaining components were separated. The filtrate was lyophilyzed (freeze-dried). Most of the peptides of the hydrolysate were in the molecular weight range of 1100 to 7500.

Keratin-containing byproducts, such as feathers, hair, bristles, horse hair, horns, cloven-hooves and hooves have long been regarded as almost worthless or even difficult waste. Nowadays, the amino acid composition of the keratin has been found useful, particularly regarding sulphur-containing amino acids, for enriching and diversifying the proteins of animal fodders. On the other hand, the amino acid content of keratin is equivalent to the amino acid composition of the human skin and hair, because skin and hair are, at least in part, composed of keratin. The keratin hydrolysate is therefore an appropriate and advantageous ingredient in cosmetic products used for caring for skin and hair. A problem related thereto is how to hydrolyse keratin into water soluble peptides of the appropriate length, or partly water soluble poly- or oligopeptides, in which the original amino acid composition will remain unchanged and which are digestible in the digestive track of animals, and which, on the other hand, are appropriate for use in the cosmetic industry.

When studying the topic in our attempts to produce a desired hydrolysate, we have come across certain problems not solved in the above-mentioned patents, nor in any other documents known to the applicant. Surprisingly, we have found that certain crucial problems, such as the small quantity of keratin-containing matter in the aqueous mixture in the pretreatment and hydrolysis stages, high salt content in the product after hydrolysis and after the end treatment, the sulphur dioxide ($SO_2$) released in the final heating on the acid side, and the poly- and oligopeptides of certain dimensions obtained directly from the hydrolysis at sufficient concentrations, can be solved relatively economically without detrimental wastes and emissions.

The invention is therefore mainly characterized by what is stated in the characteristic features part of claim 1. Therefore, it has been understood that accelerating the sulphitolysis is possible without detrimental side effects when the temperature is raised to 60° C. Thus, it is possible to shorten the pretreatment from over four hours to even less than one hour.

As taught by the invention, the first part of the enzymatic keratin hydrolysis, i.e. the denaturation of the keratin that is, opening of the sulphur bridges, is carried out chemically. It is most successful when the keratin-containing matter, such as feathers and hair, is chopped to 3 to 6 mm in an appropriate chopping machine. The chopped material is mixed in water as much as possible in a reactor. The dry-matter content of the chopped material in the mixture is advantageously about 5 to 15%. The sulphite is added into the mixture e.g. in the form of $Na_2SO_3$ for obtaining a sulphitolysis. The sulphite content varies from 5 to 25% of the dry matter and is mainly dependent on the desired degree of hydrolysis, the treatment temperature and time used. A potential oxidizing, compound, such as copper chloride or preferably a thionate is added for an oxidative sulphitolysis to modify the degree of hydrolysis caused by the enzyme treatment, in an amount of about zero to 20 per cent of the dry matter. According to one embodiment, the pH of the mixture is set to be in the range 6 to 9, preferably from 6.5 to 8.0. For setting the pH, NaOH, or preferably KOH and/or $H_2SO_4$ if preparing fodder supplement is used. The temperature is maintained at from 60° to 100° C. and the treatment time is from 10 minutes to 4 hours, preferably 10 to 60 minutes. All percentages are in w/w.

The second stage comprises the actual enzymatic treatment, i.e. the hydrolysis. This stage can be accomplished in the same reactor as the pretreatment because the feathers or hair need not be washed. The hydrolysis may be started directly after the pretreatment if the dry matter content is maintained appropriately. Stirring of the mixture is continued. The pH is controlled preferably to be in the range of 6 to 8.5. The temperature is set from 55° to 80° C., depending on the enzyme used. As for the enzyme, one proteolytic enzyme or a mixture of several proteolytic enzymes are used, the pH optimum whereof being neutral or slightly alkaline, and which are as thermally resistant as possible. Appropriate enzymes are the commercial neutral and alkaline proteases from different manufacturers derived from bacteria (e.g. Bacillus), from mildew (e.g. Aspergillus), and from plants and animals, or other suitable proteolytic enzymes. The selection of an enzyme or an enzyme mixture is, in addition to the above requirements, influenced by the length of the peptide chains of the end product. The amount of the enzyme used is determined mainly by the amount of activity required. The amount of activity is determined mainly according to the amount of substrate and the desired hydrolysis time, and it increases the shorter the time of hydrolysis desired and the greater the concentration of the substrate.

After the pretreatment stage the end product of the directly continued hydrolysis, i.e. the hydrolysate, remains too small in dry matter content to serve a number of purposes, so it has to be concentrated. This can be best accomplished by adding pretreated and filtered feathers straight into the hydrolysis the multiple-batch-straight principle. The number of additions may vary from one to three. Addition of one batch at a time is possible because after the pretreatment, the mixture of feathers and hair is easy to stir. The treatment of additional feather batches is preferably carried out in a filtrate from which the preceding feather batch has been filtered. Hereby, reactants, for instance $Na_2SO_3$ and $Na_2S_4O_6$, are recovered because only the depleted portion of the requisite reactant is added for the next treatment since not all of a reactant is used in the treatment. This is also preferable for the reason that the amount of salt in the end product remains in such instances small, only 3 to 8 per cent of the dry matter content, in comparison with the 10 to 15 per cent in the single batch hydrolysate, and the amount of $SO_2$ produced in the acid during the heating treatment of the end product remains relatively lower. The following batches are added later, as in the course of the hydrolysis the fluidity and stirrability of the mixture have again improved. In this manner, 15 to 25 per cent dry matter content of the end product is achieved.

The hydrolyzing time is determined according to the desired degree of hydrolysis when the amount of enzymatic activity and the rest of the factors are known. The most suitable hydrolysis time has proven to be 4 to 8 hours. In a multiple batch hydrolysis the use of enzyme is intensified because only in the first batch is the entire "calculated" amount of the enzyme added, and in the remaining batches only half the amount of enzyme of the preceding batch is added.

After the hydrolysis, the pH of the hydrolysate is adjusted to 2 to 5 by adding $H_2SO_4$. The pH selected depends on how much of the sulphite is removed from the mixture and how much of the keratin cysteine sulphonate (Kerat-S-$SO_3$-) is wished to be turned into the cysteine of the keratin (Kerat-S$^-$). After setting the pH, the mixture is heated to 70° to 100° C. for 15 to 45 minutes, whereby $SO_2$ is released. Most preferably the $SO_2$ release is carried out so that it is conducted into a pretreatment reactor to become $Na_2SO_3$, this being utilized in turn in the next pretreatments.

Hydrolysate meant for animal fodder is heated, preferably at 2.5 to 4.5 pH and mixed as such with fodder. The pepsine-HCl solubility of the hydrolysate thus obtained, determined as dissolved/total proteine, is 80 to 85 per cent. The salt content ($Na_2SO_4$) of the hydrolysate is 3 to 8 per cent of the dry matter in the multiple-batch hydrolysate with a dry matter content of 15 to 25 per cent, whereas the salt content is 10 to 15 per cent matter in a single-batch hydrolysate with a dry matter content of 5 to 10 per cent.

When preparing oligopeptides of certain dimensions from keratin hydrolysate, the following procedure is used. The pH of the hydrolysate, recently hydrolyzed or end-treated, is raised to 7 to 9 and the hydrolysate is heated to 80° to 90° C. for a moment, and then cooled. At that time, the proteins, precipitated at low pH, become redissolved. Thereafter the solid part is filtered off. The filtrate is microfiltered, whereby the filtrate thus obtained is sterile. Determined by the dimensions of the desired peptides the separating numbers of the ultrafilter diaphragms are selected. As an example, a sterile filtrate is ultrafiltered through a filter with a separating number of 10,000. In that instance, the permeate contains peptides smaller than 10,000 daltons. The permeate thus obtained is again ultrafiltered through a diaphragm. A keratin hydrolysate is obtained in which the dimensions of the peptides are 1,000 to 10,000 and which is at the same time concentrated to a desired concentration. In conjunction with the concentration, peptides below 1,000 dalton and other compounds and salts are washed off. In the end treatment of the hydrolysate, while heating in acid, the cysteine sulphonates of the oligopeptides become respective cysteines with the extraction of $SO_2$. In conjunction with ultrafiltration, when washing the concentrate, the salt content is reduced. Then sulphur bridges are again produced between the cysteines of the peptides in the alkaline and oxidizing environment. The concentration of the end product is stabilized during the ultrafiltration. The end product may also be dry, which may be accomplished by freeze drying, jet drying or vacuum drying.

The following examples illustrate the above-described invention.

EXAMPLE 1

215 kg of chopped feathers, dry weight about 60 kg, were mixed into a uniform mixture in 735 liters of water in a 2,000 liter reactor. 4.8 kg of $Na_2SO_3$ were added into the mixture and the pH was set to 7.5. Stirring constantly the mixture was heated to 95° C. and maintained thereat for 40 minutes.

After the above treatment, the mixture was cooled to 60° C. and the pH was set to 8.0, and this pH was maintained with KOH. For the enzyme used in the hydrolysis, a proteolytic bacteria-derived enzyme (Maxatase, Gist-Brocades, Netherlands) was used. The mixture was stirred continuously so that the entire mass was moving and became well mixed.

The hydrolysis lasted 6 hours. Thereafter the pH was set to 4.0 with $H_2SO_4$. Simultaneously, about 25 liters per minute of filtered air were conducted through the reactor. The $SO_2$ thus produced was in this manner conducted to a second reactor in which it was dissolved in water in the form of $Na_2SO_3$. After the thermal treatment the hydrolysate was cooled to 60° C. and packed into plastic containers.

The raw protein of the hydrolysate of the dry matter was 80 5%, and 14.5% ash, the pepsin HCl solubility (soluble/total protein), was 82%.

EXAMPLE 2

1.0 kg of chopped feathers of 28% dry matter content was mixed in water and 28.0 g of $Na_2O_3$ and 23.0 g of $Na_2S_4O_6$ were added in the mixture. The pH was set to 8.0. The mixture was heated to 80° C. and maintained thereat for 30 minutes while stirring.

After this treatment, the mixture was cooled to 65° C. the and pH was set to 7.0 and this pH was maintained with NaOH. For the enzyme, pepsin was used (Profix, Biocon, Ireland), its amount being so calculated that 4 hours were enough for the hydrolyzing time. The mixture was stirred strongly throughout the hydrolysis. Upon the completion of the hydrolysis step, the pH of the mixture was maintained at 7.0, and it was heated to 90° C. for a moment to destroy the enzymatic activity. Thereafter the mixture was cooled to 35° C. The solid ingredients were filtered off from the mixture and the clear filtrate was ultrafiltered with diaphragms of 10,000 separating number. Only a very small portion became concentrated during the filtering, and therefore, most of it was filtered through as a permeate. In the next stage the permeate thus obtained was concentrated and washed with ultrafiltering, the separating number of the diaphragms used being 1,000. The concentrate was washed until all penetrating peptides were removed and the salt content was one tenth of the original.

Finally, the hydrolysate was so concentrated that the end product was a semifluid and rather light solution. Part of this solution was freezedried in small bottles.

EXAMPLE 3

1.5 kg of chopped pig bristles were mixed in 5.0 liters of water. 40 g of $NaHSO_3$ and 10.0 g of $Na_2S_4O_6$ were added to the mixture. The pH was set to 6.5 and the mixture was heated to 90° C. and maintained thereat for 30 minutes. After this denaturation the mixture was cooled to 60° C. and the pH was set to 7.0 and maintained thereat with KOH. For the enzyme, a mixture containing two thirds bacteria-originated proteolytic enzyme (Alcalase, Novo, Denmark) and one third pepsin (Profix, Biocon, Ireland) was used. The enzymes were added separately. Such amount of the enzyme mixture was added that the hydrolysis lasted 4 hours. The hair mixture was mixed throughout the hydrolysis.

Upon the completed hydrolysis, the pH of the mixture was still maintained at 7.0. The mixture was heated for a moment to 90° C. in order to inactivate the enzyme and then cooled to 35° C. The treatment of the hydrolysate into end products was carried out as in Example 3.

EXAMPLE 4

1.0 kg chopped feathers (dry matter 27%) was mixed in 3 l of water and then more water was added so that the total volume was 5.0 l. The mixture was stirred efficiently. 30.0 g of $Na_2SO_3$ was added in the mixture, and the pH was set to 7.5. The mixture was heated to 95° C. and maintained thereat for 30 minutes. After the denaturation the mixture was cooled to 60° C. and the solid part filtered off from the solution. The solid part was stored for the hydrolysis. The filtered solution, i.e. filtrate, was returned to the reactor and a second 1.0 kg batch of the same feathers and enough water were added so that the end volume of the mixture was 5.0 liter. The mixture was stirred and only 15.0 g of $Na_2SO_3$ were added because the filtrate already contained free $SO_3^{-2}$. The mixture was heat-treated and filtered in the same way as the first batch. The filtrate of the second batch was returned again into the reactor and a third batch, 1.0 kg of the same feathers as before and so much water was added that the end volume of the mixture was 5.0 liter. $Na_2SO_3$ was added and the mixture was treated in the same way as the second batch.

The hydrolysis of the denatured feathers was carried out so that 1.0 liter of the filtrate from the third treatment batch was added to the reactor, and the solid part of the feathers of the same batch, separated by filtration was added and stirred efficiently. In order to ensure adequate mixing, 0.5 liter of the same filtrate was added, the pH was set to 7.5 and it was maintained at that value with NaOH. For the enzyme a commercial proteolytic enzyme (Alcalase, Novo, Denmark) was used and so much of it was added that the hydrolysis took place in 4 hours. After one hour of hydrolysis, the filtered solid part of feathers from the second pretreatment batch was added. The hydrolysis was continued under the same conditions. Half of the enzyme amount of the second batch was added. After the last addition, the hydrolysis was continued for 4 hours. After the hydrolysis, the hydrolysate was treated as in Example 1, with the exception that $SO_2$ was not removed by means of an air current. In the finished hydrolysate the dry matter content was 19% and the ash content of the dry matter 8.5%.

I claim:

1. A process for hydrolyzing keratin comprising:
   (a) pretreating a solid keratin ingredient in an aqueous solution containing sulphite ions so as to denature the keratin, the solution containing an amount of sulphite ions which is the same as the amount of sulphite ions obtained from using an amount of $Na_2SO_3$ which is from about 5% to about 25% (weight/weight) of the amount of the dry keratin ingredient, the pretreatment being performed at a pH of from about 6 to about 9, at a temperature from about 60° to about 100° C., for about 10 minutes to about 4 hours; and
   (b) then hydrolyzing the pretreated keratin with a proteolytic enzyme, the hydrolysis being carried out by sequentially adding portions of the pretreated keratin to the enzyme as the hydrolysis proceeds.

2. A process according to claim 1 wherein the pretreatment (a) is performed at a pH of from about 6.5 to about 8.

3. A process according to claim 1 wherein the pretreatment (a) is performed at a temperature of about 75° to about 100° C.

4. A process according to claim 1 wherein the pretreatment (a) is performed for about 10 minutes to about 60 minutes.

5. A process according to claim 1 wherein sodium sulphite is used as the source of the sulphite ions.

6. A process according to claim 1 or claim 5 wherein several portions of the pretreated keratin ingredient from step (a) are sequentially added to the enzyme during hydrolysis step (b) until the dry content of the enzyme hydrolysate is from about 15 to about 25% by weight.

7. A process according to claim 5 wherein the aqueous solution used for the pretreatment also contains an alkali metal thionate.

8. A process according to claim 7 wherein the alkali metal thionate is sodium tetrathionate.

9. A process according to claim 1 wherein the pretreatment (a) is carried out so that the dry matter content of the keratin ingredient in the aqueous solution is from about 5 to 15 per cent by weight.

10. A process according to claim 1 wherein the aqueous solution containing the sulphite ions is used for the pretreatment of several batches of solid keratin ingredient.

11. A process according to claim 1 wherein the product of the pretreatment step (a) is hydrolyzed according to step (b) without intervening steps.

12. A process according to claim 1 wherein the proteolytic enzyme used in step (b) has a pH optimum which is neutral or slightly alkaline and is thermally resistant.

13. A process according to claim 12 wherein the enzyme is a bacterial, fungal, plant or animal protease.

14. A process according to claim 1 wherein the hydrolysis step (b) is carried out at a temperature from about 55° to about 80° C.

15. A process according to claim 1 wherein the pH is maintained at from about 6.0 to 8.5 during the hydrolysis step (b).

16. A process according to any one of claims 1-5 or 7-15, comprising the additional step of:
   (c) adjusting the pH of the product of hydrolysis step (b) to from about 2 to about 5 and then heating it to from about 70° to about 100° C. for about 15 to about 45 minutes.

17. A process according to claim 16, comprising the additional steps of:
   (d) heating the product of step (c) while maintaining the pH at from about 2.5 to about 4.5; and
   (e) mixing the resultant product in animal fodder.

18. A process according to claim 17, wherein the $SO_2$ released during step (d) is recycled and used in step (a).

19. A process according to any one of claims 1-5 or 7-15 comprising the additional steps of:
   (c) adjusting the pH of the product of step (b) to from about 7 to about 9;
   (d) then heating it to from about 80° to about 90° C.; and
   (e) filtering off the solids and using them to produce oligopeptides of a given size.

* * * * *

UNITED STATES PATENT AND TRADEMARK OFFICE
CERTIFICATE OF CORRECTION

PATENT NO. : 5,262,307
DATED : November 16, 1993
INVENTOR(S) : JOUKO E. T. SAVOLAINEN It is certified that error appears in the above-indentified patent and that said Letters Patent is hereby corrected as shown below:

Column 1, line 4, after "The" please insert --present--.

Column 1, line 6, after "sulphite" please delete ".".

Column 1, line 7, please delete "then and" and substitute therefor --and then--.

Column 1, line 36, please delete "lantionine" and substitute therefor --lanthionine--.

Column 2, line 5, after "the" please insert --dry--.

Column 2, line 11, please delete "cystine" and substitute therefor --cysteine--.

Column 2, line 18, please delete

"kerat-S-S-kerat plus 2 + 2$SO_3^{-2}$ + $S_4O_6^{-2}$"

and substitute therefor

--kerat-S-S-kerat + 2 $SO_3^{-2}$ + $S_4O_6^{-2}$ ----> --.

Column 2, line 23, please delete "17133-1739" and substitute therefor --1713-1739--.

Column 2, line 34, after "hydrolysis" please delete "the".

Column 2, line 57, please delete "lyophilyzed" and substitute therefor --lyophilized--.

Column 4, line 22, after "hydrolysis" please insert --underway by--.

UNITED STATES PATENT AND TRADEMARK OFFICE
CERTIFICATE OF CORRECTION

PATENT NO. : 5,262,307
DATED : November 16, 1993
INVENTOR(S) : JOUKO E. T. SAVOLAINEN It is certified that error appears in the above-indentified patent and that said Letters Patent is hereby corrected as shown below:

Column 4, line 23, please delete "straight" and substitute therefor --batch--.

Column 4, line 57, please delete "Kerat-S-So$_3$-" and substitute therefor --Kerat-S-SO$_3$- --.

Column 5, line 4, before "matter" please insert --of the dry--.

Column 5, line 63, please delete "80 5%" and substitute therefor --80.5%--.

Column 5, line 63, after "ash," please insert --and--.

Column 6, line 5, before "and" please delete "the".

Column 6, line 6, please delete "pepsin" and substitute therefor --papain--.

Column 6, lines 38-39, please delete "pepsin" and substitute therefor --papain--.

Signed and Sealed this

Sixth Day of September, 1994

Attest:

BRUCE LEHMAN

Attesting Officer   Commissioner of Patents and Trademarks